United States Patent [19]

Berger et al.

[11] Patent Number: 5,192,463
[45] Date of Patent: Mar. 9, 1993

[54] LOW TEMPERATURE, POLYPHENYLMETHANE-BASED DIELECTRIC COMPOSITIONS

[75] Inventors: Noelle Berger, Ecully; Raymond Commandeur, Vizille; Pierre Jay, Didier Au Mont D'Or,, all of France

[73] Assignee: Atochem, Puteaux, France

[21] Appl. No.: 750,702

[22] Filed: Aug. 20, 1991

Related U.S. Application Data

[63] Continuation of Ser. No. 481,639, Feb. 20, 1990, abandoned.

[30] Foreign Application Priority Data

Feb. 20, 1989 [FR] France .................. 89/02166

[51] Int. Cl.$^5$ .......... C11D 1/18; C11D 7/72; C09D 9/00; H01B 3/24
[52] U.S. Cl. ................... 252/570; 252/153; 252/162; 252/171; 252/172
[58] Field of Search ............... 252/570, 162, 171, 172, 252/153

[56] References Cited

U.S. PATENT DOCUMENTS 4,523,044  6/1985  Commandeur et al. .............. 585/11

FOREIGN PATENT DOCUMENTS 0136230  9/1984  European Pat. Off. .
0299866  1/1989  European Pat. Off. .
0299867  1/1989  European Pat. Off. .

Primary Examiner—A. Lionel Clingman
Assistant Examiner—William S. Parks
Attorney, Agent, or Firm—Burns, Doane, Swecker & Mathis

[57] ABSTRACT

Novel dielectric compositions, well adapted for low temperature applications, include admixture of benzyltoluene, benzylbenzene and the higher homologs thereof, and optionally contain triphenylmethane, ditolylphenylmethane, tolyldiphenylmethane and the higher homologs thereof; the subject novel compositions are prepared by chlorinating a mixture of toluene and benzene and then treating the product of reaction with an inorganic halide.

16 Claims, No Drawings

LOW TEMPERATURE, POLYPHENYLMETHANE-BASED DIELECTRIC COMPOSITIONS

This application is a continuation of application Ser. No. 07/481,639, filed on Feb. 20, 1990, now abandoned.

BACKGROUND OF THE INVENTION

1. Field of the Invention

The present invention relates to novel compositions of matter based on polyphenylmethanes, to a process for the preparation thereof, and to the use of such novel compositions as a dielectric material.

This invention especially relates to admixtures of mono- and dibenzyltoluene, and mono- and dibenzylbenzene, such admixtures optionally comprising triphenylmethane, ditolylphenylmethane, tolyldiphenylmethane, or the higher homologs thereof.

2. Description of the Prior Art

Patent Application EP 259,798 describes mixtures of monobenzyltoluene, ethylbiphenyl and/or 1,1-diphenylethane with other biphenyls or other diphenylmethanes containing not more than 17 carbon atoms.

Patent Application EP 262,456 describes mixtures of monobenzyltoluene and of a diphenylmethane substituted by alkyl groups, with the overall molecule containing from 15 to 17 carbon atoms.

Patent Application EP 172,537 describes mixtures of benzylbenzene isomers.

And Patent Application EP 282,083 describes mixtures of monobenzyltoluene and of ditolylmethane.

All of these prior art compositions are prepared by addition or coupling reactions of pure reactants, which necessitate a difficult separation stage.

Patent Application EP 136,230 describes mixtures of monobenzyltoluene, dibenzyltoluene and ditolylphenylmethane which can be employed as dielectric fluids. It also describes a very simple process for preparing such mixtures.

SUMMARY OF THE INVENTION

A major object of the present invention is the provision of novel compositions based on the polyphenylmethanes which have improved dielectric properties vis-a-vis the prior art mixtures, which novel compositions are well adapted for low temperature applications.

Another object of the present invention is the provision of a simple and effective process for the preparation of such novel compositions Briefly, the present invention features novel dielectric compositions comprised of the two oligomers $A_1$ and $A_2$, wherein:

(i) $A_1$ is an isomer or a mixture of isomers of the formula:

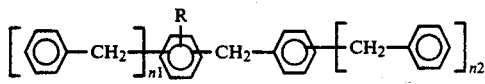

in which $n_1$ and $n_2 = 0$, 1 or 2, with the proviso that $n_1 + n_2$ is less than or equal to 3 and R is a hydrogen atom; and (ii) $A_2$ is an isomer or a mixture of isomers having the same general formula as $A_1$, except that R is methyl and $n_1$ and $n_2$ are designated as $q_1$ and $q_2$ but have the same definition, and with the further proviso that at least one of the oligomers $A_1$ and $A_2$ comprises an isomer having three benzene nuclei.

DETAILED DESCRIPTION OF THE PREFERRED EMBODIMENTS OF THE INVENTION

More particularly according to the present invention, the oligomer $A_2$ advantageously comprises, for example, metabenzyltoluene, or a mixture of two isomers of benzyltoluene, or a mixture of the three isomers of benzyltoluene. It may also comprise a well-defined isomer with $q_1 = 1$ and $q_2 = 0$, such as 3,5-dibenzyltoluene, or a mixture of all of the isomers such that $q_1 = 1$ and $q_2 = 0$ or a mixture of isomers such that $q_1 = 0$ and $q_2 = 1$.

$A_2$ also advantageously comprises a mixture of isomers in which $q_1$ and $q_2$ have a number of values, for example a mixture of 64% by weight of dibenzyltoluene, 22% by weight of the mixture of isomers such that $q_1 + q_2 = 1$, 10% by weight of the mixture of isomers such that $q_1 + q_2 = 2$ and 4% by weight of the mixture of isomers such that $q_1 + q_2 = 3$. $A_2$ may also comprise any combination of the isomers or mixtures of isomers described above.

The immediate above also applies to the oligomer $A_1$. $A_2$ is therefore an isomer or a mixture of isomers of benzylbenzene, or of its higher homologs. The composition according to the invention is such that at least one of the oligomers $A_1$ or $A_2$ is an isomer which has at least 3 benzene nuclei in its molecular structure or a mixture of isomers which has 3 benzene nuclei, or a mixture comprising at least one isomer or isomers having 3 benzene nuclei.

The compositions of the invention may comprise a mixture of any one oligomer $A_1$ with the oligomer $A_2$ comprising either dibenzyltoluene, namely, one or more isomers in which $q_1 = 1$ and $q_2 = 0$, or tolyl(benzylphenyl)methane, methane, namely, one or more isomers in which $q_1 = 0$ and $q_2 = 1$.

The compositions of the invention advantageously comprise one of the following combinations of the oligomers $A_1$ and $A_2$:

(a) $A_1$ wherein $n_1 = n_2 = 0$
  $A_2$ wherein $q_1 + q_2 = 1$;
(b) $A_1$ wherein $n_1 + n_2 = 1$
  $A_2$ wherein $q_1 = q_2 = 0$;
(c) $A_1$ wherein $n_1 + n_2 = 1$
  $A_2$ wherein $q_1 + q_2 = 1$.

Although the proportions of $A_1$ and $A_2$ may be any value whatsoever, the amount of $A_2$ is advantageously greater than the amount of $A_1$ and preferably ranges from 60% to 80% by weight of the total amount of $A_1$ and $A_2$.

The compositions of the present invention based on the two oligomers $A_1$ and $A_2$ may additionally comprise at least one oligomer selected from among the following oligomers $B_1$, $B_2$ and $B_3$:

(iii) $B_1$ is an isomer or a mixture of isomers of the formula:

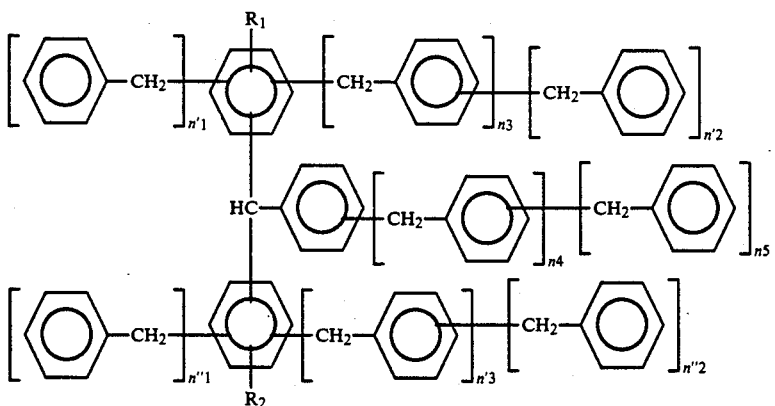

in which $n'_1$, $n''_1$ and $n_4 = 0$, 1 or 2 and $n'_2$, $n''_2$, $n_3$, $n'_3$ and $n_5 = 0$ or 1, with the proviso that $n'_1 + n''_1 + n'_2 + n''_2 + n_3 + n'_3 + n_4 + n_5$ is less than or equal to 2; and $R_1$ and $R_2$ are each a hydrogen atom;

(iv) $B_2$ is an isomer or a mixture of isomers having the same general formula as $B_1$, except that $R_1$ and $R_2$ are each methyl and the coefficients n are designated as q but have the same definition; and (v) $B_3$ is an isomer or a mixture of isomers having the same general formula as $B_1$, except that $R_1$ and $R_2$ are different, one being a hydrogen atom and the other methyl and the coefficients n are designated as r, but have the same definition.

The oligomer $B_1$ in its simplest form is triphenylmethane. It may also comprise a well-defined isomer of (benzylphenyl)diphenylmethane, namely, $n'_1 = 1$ and all of the other coefficients have the value of zero, or a mixture of a plurality of isomers of such oligomer. $B_1$ may also comprise a mixture of isomers in which the coefficients n have different values, for example such that 72% by weight of $B_1$ comprises isomers, the sum of which: $n'_1 + n''_1 + n'_3 + n_3 + n'_2 + n''_2 + n_4 + n_5$ has the value 0; 21% by weight of $B_1$ comprises isomers whose above sum has the value of 1; and the remainder comprises isomers whose above sum has the value 2. $B_1$ may also comprise an isomer or a mixture of isomers represented by a well-defined set of coefficients n. It may also comprise a mixture which is a combination of two or more of the aforementioned mixtures. The oligomers $B_2$ and $B_3$ are defined in the same manner.

Particularly advantageous compositions of this invention comprise $A_1$, $A_2$ and $B_2$. Among such compositions, the following are the preferred:

(a) $A_1$ wherein $n_1 = n_2 = 0$
$A_2$ wherein 60% to 90% by weight of
$A_2$ comprises isomers in which $n_1 = n_2 = 0$
Any $B_2$;
(b) $A_1$ wherein more than 50% by weight of
$A_1$ comprises isomers in which $n_1 + n_2 = 0$
$A_2$ and $B_2$ as in (a).

Among the compositions based on $A_1$, $A_2$ and on at least one of the oligomers $B_1$, $B_2$ and $B_3$, that comprising the 5 oligomers $A_1$, $A_2$, $B_1$, $B_2$ and $B_3$ is particularly advantageous and is unexpectedly very easy to produce.

Similarly preferred compositions of the present invention comprise the mixture $A_1$, $A_2$, $B_1$, $B_2$.

All of the compositions described above can be employed as a dielectric fluid, in particular for capacitors. These compositions may be purified, for example by being contacted with a decolorizing earth, a bentonite or an equivalent product until a sufficiently high resistivity is attained and can generally be purified using the conventional techniques for purifying liquids intended for dielectric application. Conventional additives for dielectric liquids may also be added to the compositions of the invention, such as epoxides or antioxidants of the di-tert-butyl-para-cresol type, or anthraquinone derivatives.

The present invention also features various processes for the synthesis or production of the above compositions.

The oligomers $A_1$ and $A_2$ may be prepared by reacting benzyl chloride $C_6H_5CH_2Cl$ with toluene in the case of $A_2$, and with benzene in the case of $A_1$. As regards the oligomers $B_1$, $B_2$ and $B_3$, these may be prepared by reacting benzylidene chloride $C_6H_5CHCl_2$ with benzene, toluene, benzyl chloride and the oligomers $A_1$ and $A_2$.

Benzyl chloride and benzylidene chloride are of course known compounds. For example, radical chlorination of toluene can be carried out, followed by a distillation to separate the $C_6H_5CH_2Cl$ and $C_6H_5CHCl_2$.

Next, when the various oligomers A and B have been prepared, it suffices to admix them to formulate the compositions of the invention.

A particularly convenient technique for obtaining the mixture of the oligomers $A_2$ and $B_2$ is described in European Patent EP 136,230 and entails, in a first stage, reacting chlorine with toluene via radical reaction in the presence of a free radical generator and, in a second stage, subjecting the product of reaction of the first stage to the action of an inorganic halide or of an inorganic acid.

A process for preparing $A_1 + B_1$ comprises:
(a) reacting chlorine with a mixture of benzene and toluene via radical reaction in the presence of a free radical generator;
(b) removing the unreacted toluene; and
(c) subjecting the resulting product to the action of an inorganic halide or of an inorganic acid.

The radical chlorination of the mixture of benzene and toluene is usually carried out at a temperature ranging from 50° to 110° C., preferably from 70° to 100° C. It is preferably conducted such that only 10% to 40% of the toluene introduced, expressed as a molar percentage, is converted into the corresponding chlorinated derivative. Either a photochemical initiation or a chemical initiator may be employed as a free radical generator; representative chemical initiators include azo compounds such as azodiisobutyronitrile or azodivaleronitrile, and the peroxides, such as, for example, lauroyl peroxide. The amount of chemical initiator employed generally ranges from 0.05% to 3% by weight relative to the toluene introduced, and preferably from 0.1% to 1.5%.

It has now surprisingly been determined that if the benzene/toluene mixture contains at least 15 mol % of toluene and preferably from 20% to 30%, no chlorination of the benzene occurs.

The toluene is then removed, for example by distillation using one or more columns and with the benzene, which might exit with the unchlorinated toluene, being returned to the reaction mixture which contains the chlorinated toluene.

The reaction mixture obtained during the preceding stage, i.e., a mixture of $C_6H_6$, $C_6H_5CH_2Cl$ and $C_6H_5CHCl_2$, is next subjected to the action of an inorganic halide or of an inorganic acid. In practice, this reaction is carried out at a temperature of from 30° to 110° C. and preferably from 50° to 100° C. Exemplary inorganic halides include ferric chloride, antimony trichloride, titanium tetrachloride or aluminum chloride, in weight proportions relative to the reaction mixture which typically range from 50 ppm to 1% and preferably from 100 ppm to 0.5%. Inorganic acids may also be employed, for example sulfuric acid at a weight concentration ranging from 70% to 95%. It is also possible to employ zeolites or certain inorganic oxides.

An alternative embodiment of this second stage of the process comprises pouring the reaction mixture from the first stage into a fraction of benzene or of benzene and the mixture of oligomers according to the invention, containing the inorganic halide or acid in solution or dispersion. This alternative embodiment is of particular interest where such a lo process is carried out continuously, it being apparent that such synthesis could be carried out either discontinuously or continuously.

After distillation of the excess benzene, it is recommended to remove the inorganic halide or the inorganic acid by any known means, such as Washing with water, neutralizing and drying.

$A_1 + B_1$ can also be prepared according to a variant of the above process in which benzene is introduced after the chlorination of toluene.

Such process comprises:

(a) reacting chlorine with toluene via radical reaction in the presence of a free radical generator;

(b) removing the unreacted toluene; and (c) adding benzene and subjecting the resulting product to the action of an inorganic halide or of an inorganic acid.

This process is carried out in the same manner as in the preceding case where a mixture of toluene and benzene is chlorinated; on the other hand, the removal of toluene is much easier because it is the most volatile compound.

It is also within the ambit of the invention to replace the stages (a) and (b) with a synthesis of a mixture of $C_6H_5CH_2Cl$ and $C_6H_5CHCl_2$.

The invention also features a process for preparing the mixture of oligomers $A_1 + A_2$, comprising contacting benzyl chloride with benzene and toluene in the presence of an inorganic halide or of an inorganic acid.

This reaction is carried out under the same conditions as those described above for stage (c) of the processes for preparing $A_1 + B_1$.

It is also possible to prepare $A_1 + A_2$ using an alternative embodiment of the above process, comprising:

(a) reacting chlorine with toluene and benzene in the presence of a free radical generator;

(b) removing benzylidene chloride; and (c) subjecting the resulting product to the action of an inorganic halide or of an inorganic acid.

The implementation of such process is akin to the preceding syntheses. In the case of stage (b), it is advantageous to employ distillation, for example by collecting the light fraction of the mixture obtained in (a). This light fraction includes benzene, toluene and benzyl chloride; it then suffices to add thereto (i) an inorganic halide or an inorganic acid or (ii) a product containing this halide or this acid.

It is also within the ambit of the invention to carry out stage (a) without benzene and to add it at stage (c). Toluene also may be added in the stage (c).

This invention also features a process for preparing the mixture of the oligomers $A_1$, $A_2$, $B_1$, $B_2$ and $B_3$, comprising:

(a) reacting chlorine with a mixture of benzene and toluene via radical reaction in the presence of a free radical generator; and (b) subjecting the resulting reaction product to the action of an organic halide or of an inorganic acid. As above, provided the benzene/toluene mixture contains at least 15 mol % of toluene, no chlorination of benzene occurs. The implementation of such latter process is similar to the above embodiments.

In order to further illustrate the present invention and the advantages thereof, the following specific examples are given, it being understood that same are intended only as illustrative and in nowise limitative.

EXAMPLE 1

The testing in this Example entailed subjecting models of capacitors to accelerated aging at elevated voltage and temperature.

The principal criterion in the tests was the number of capacitors which failed. In some of the tests, the aging period was short and the measurement of the dielectric strength of the capacitors which had not failed during the test yielded additional information on the deterioration of the insulation.

I. Test on Mixed Capacitors

Two series of ten capacitors were manufactured for this test, comprising two layers of smooth polypropylene film 12 μm in thickness and a layer of relative density 1.0 and 12 μm in thickness.

These two series of capacitors were impregnated, one with an oligomer $A_2$ such that 75% by weight was benzyltoluene ($q_1 = q_2 = 0$) and 25% by weight isomers such that $q_1 + q_2 = 1$ and containing bisphenol A diglycidyl ether in the proportion of 1 part to 100 parts of $A_2$, the other with a mixture of $A_1$ and $A_2$ such that:

(a) $A_2$ represented 70% by weight of $A_1 + A_2$;

(b) $A_1$ comprised 70% by weight of isomers such that $n_1 = n_2 = 0$ and 30% by weight of isomers such that $n_1 + n_2 = 1$.

1.1. Endurance

After impregnation and thermal forming, the capacitors were subjected to aging at 85° C. under 2,700 V (75 V/μm) for 535 hours. After this first aging, no failure having been observed, the test was continued under 3,000 V (83.8 V/μm) in order to increase its severity.

After 4,400 hours of aging, the following results were obtained:

| Time under voltage (hours) | Number of surviving capacitors | |
|---|---|---|
| | $A_2$ | $A_1 + A_2$ |
| 0 | 10 | 10 |
| 695 | 9 | 10 |
| 1,056 | 8 | 10 |
| 1,458 | 7 | 10 |
| 3,290 | 5 | 10 |
| 3,450 | 5 | 9 |
| 3,915 | 5 | 8 |
| 3,990 | 5 | 7 |
| 4,400 | 5 | 7 |

These results favored the mixture $A_1 + A_2$.

1.2. Changes in tan δ

The tan δ of the capacitors was measured after 535, 1,460 and 4,400 hours of aging.
The following results were obtained:

| Aging period (hours) | Measurement voltage (volts) | Tan δ × $10^{-4}$ (85° C.) | |
|---|---|---|---|
| | | $A_2$ | $A_1 + A_2$ |
| 535 | 5,000 | 5.9 | 5.7 |
| | 1,000 | 6.1 | 5.6 |
| | 2,000 | 6.4 | 5.9 |
| | 3,000 | 7.9 | 7.0 |
| 1,460 | 500 | 9.0 | 6.4 |
| | 1,000 | 9.4 | 6.5 |
| | 2,000 | 10.3 | 6.8 |
| | 3,000 | 12.5 | 8.1 |
| 4,400 | 500 | 4.6 | 4.1 |
| | 1,000 | 4.6 | 4.2 |
| | 2,000 | 4.9 | 4.4 |
| | 3,000 | 5.9 | 4.9 |

The tan δ of the capacitors impregnated with the mixture $A_1 + A_2$ was significantly lower than that of the capacitors impregnated with $A_2$, evidencing that the deterioration was less pronounced.

II. Tests on All-Film Capacitors

Three series of ten capacitors were manufactured for this test, each comprising two layers of rough polypropylene film with a weight thickness of 13.5 μm.

Two series were impregnated with the above oligomer $A_2$, and one series was impregnated with the above mixture $A_1 + A_2$.

2.1. Endurance

After impregnation and thermal forming, these capacitors were subjected to aging at 90° C. under 2,400 V (88.9 V/μm) for 500 hours.
The following results were obtained:

| Time under voltage (hours) | Number of surviving capacitors | |
|---|---|---|
| | $A_2$ | $A_1 + A_2$ |
| 0 | 20 | 10 |
| 160 | 19 | 10 |
| 188 | 18 | 10 |
| 259 | 17 | 10 |
| 418 | 17 | 9 |
| 479 | 16 | 9 |
| 500 | 16 | 9 |

These results showed a slight difference in favor of the mixture $A_1 + A_2$.

2.2. Change in the breakdown voltage

To confirm these results, the breakdown voltage of the capacitors which still survived at the end of the aging test was measured.

The same measurement, performed on new capacitors, gave a value of 11.5 kV. Any deterioration in the insulation during the aging is reflected in a drop in the dielectric strength.

The following results were obtained;
(i) capacitors impregnated with $A_2$: 6.6 kV
(ii) capacitors impregnated with $A_1 + A_2$: 9.4 kV.

These results clearly evidenced that the deterioration of the capacitors impregnated with $A_1 + A_2$ was much smaller.

EXAMPLE 2

Synthesis of an oligomer $A_1$ 54 moles of benzene (4,212 g) and 1 g of $FeCl_3$ were charged into a 6-liter reactor fitted with a rotary stirrer, a reflux condenser, a nitrogen injector and a dropping funnel. The mass in the reactor, blanketed with nitrogen, was heated to 65° C. 6 moles of benzyl chloride (759 g) were introduced via the dropping funnel over 4 hours. The reaction mixture was maintained stirred for another 1 hour and 0.25 g of $FeCl_3$ were added. The reaction mixture was maintained at 70° C. for another 2 hours under a stream of nitrogen. The quantity of hydrochloric acid released was 5.95 moles. The unreacted benzene was then removed by a simple distillation. The crude polyphenylmethane (873 g) was then treated with 1% of anhydrous $Na_2CO_3$ for 3 hours at 275° C. under stirring. After treatment, the product was subjected to a distillation with a column 30 cm in height, filled with a packing consisting of glass helices, under a vacuum of 1 mm of mercury.

The fraction of compounds containing two aromatic rings distilled over at about 85° to 95° C.

The fraction of compounds containing three aromatic rings distilled over at about 170° to 200° C.

The fraction of compounds containing four aromatic rings distilled over at about 260° to 280° C. (after the distillation column had been removed).

The residue represented 5.8% of the material introduced. The distillation fractions were mixed and represented 94% of the starting material. An oligomer $A_1$ was obtained, whose composition by weight was the following:

| | |
|---|---|
| $n_1$ and $n_2 = 0$ | 66.5% |
| $n_1 = 1$, $n_2 = 0$ | 27% |
| $n_1$ and $n_2 = 1$ | 6.5% |

The characteristics of the composition were as follows:

| |
|---|
| Crystallization point = +3° C. |
| Viscosity at 40° C. = 3.4 cP |
| Viscosity at 20° C. = 5.8 cP |
| Relative density at 40° C. = 1.001 |
| Relative density at 20° C. = 1.012. |

EXAMPLE 3

Synthesis of the mixture $A_1+B_1$ 9.61 moles of benzyl chloride (1,266 g) and 0.306 moles of benzylidene chloride (1,266 g), which was obtained by photochlorination of toluene (toluene/chlorine molar ratio $=4$) and separation of the unreacted toluene by distillation, were placed in the dropping funnel in an apparatus identical with that of Example 2.

This material was reacted under the same conditions as in Example 2 with 50 moles of benzene (3,900 g) and 1 g of $FeCl_3$. The hydrochloric acid collected was 9.99 moles. The product obtained after distillation of the unreacted benzene represented 1,304 g. It was treated with sodium carbonate as in Example 2 and was then subjected to the same distillation. The distillation residue represented 14.2% of the material introduced. The fractions were mixed and represented 85% of the material introduced. The product thus obtained was a mixture of oligomers $A_1$ and $B_1$.

It contained, on a weight basis:

(i) 53% of oligomers $A_1$ $n_1$ and $n_2=0$;

(ii) 31% of oligomers $A_1$ $n_1=1$, $n_2=0$ and of oligomers $B_1$ $n'_1=n_2=n''_1=n''_2=n_3=n'_3=n_4=n_5=0$.

(iii) 16% of oligomers $A_1$ $n_1=n_2=1$ and of oligomers $B_1$ $n'_1+n'_2+n''_1+n''_2+n_3+n'_3+n_4+n_5=1$.

Its characteristics were as follows:

| | |
|---|---|
| Crystallization point | $-15°$ C. |
| Viscosity at 20° C. | 8.1 cP |
| Relative density at 20° C. | 1.019. |

EXAMPLE 4

Preparation of $A_1+A_2+B_1+B_2+B_3$ 5 moles of benzene (390 g) and 5 moles of toluene (460 g) were placed in a 1—1 reactor fitted with a stirrer, a condenser, a chlorine feed tube and a 30-watt Philips TLADK lamp arranged externally; 1.25 moles of chlorine (78.1 g) was then introduced while the temperature was maintained at 85° C. for 1 hour. The quantity of hydrochloric acid released was 1.15 moles. Chromatographic analysis showed that the benzene was perfectly inert during the chlorination. The mixture contained 16% of benzyl chloride and 0.52% of benzylidene chloride by weight.

The reaction mixture was placed in a dropping funnel and was introduced over 1 hour into a 1—1 reactor fitted with a rotary stirrer, containing 0.166 moles of toluene (15.3 g), 0.166 moles of benzene (12.95 g) and 0.15 g of $FeCl_3$ at a temperature of 80° C. The entire mass was maintained at 80° C. for another 1 hour with nitrogen purging. The quantity of hydrochloric acid released was 1.1 moles.

The product obtained after distillation of the benzene and of the unreacted toluene represented 180 g. It was treated with sodium carbonate as in Example 1 and was subjected to the same distillation. The distillation residue represented 2.76% of the material introduced. The distillation fractions were mixed and represented 97.1% of the material introduced. The product thus obtained was a mixture of oligomers $A_1$, $A_2$, $B_1$, $B_2$ and $B_3$:

| | | |
|---|---|---|
| (i) 71.1% of oligomer $A_1 + A_2$ | $n_1$ and $n_2 = 0$ | |
| (ii) 24.3% of oligomer $A_1 + A_2$ | $n_1 = 1$ and $n_2 = 0$ | $q_1$ and $q_2 = 0$; $q_1 = 1$ and $q_2 = 0$ and | of oligomers $B_1+B_2+B_3$ such that all the coefficients n, p and r were zero;

| | | |
|---|---|---|
| (iii) 4.6% of oligomers $A_1 + A_2$ | $n_1 = n_2 = 1$ $q_1 = q_2 = 1$ and | | of oligomers $B_1+B_2+B_3$ such that the sum of all the coefficients n was equal to 1, the sum of all the coefficients q was equal to 1, and the sum of all the coefficients r was equal to 1.

In the oligomer $A_1+A_2$, the weight distribution between $A_2$ was 85/15 (determined by gas phase chromatography) for the value $n_1$ and $n_2=0$.

Its characteristics were as follows:
Crystallization at $<-32°$ C.
Viscosity at 20° C.$=6.7$ cP
Relative density at 20° C. $=0.998$.

EXAMPLE 5

Several mixtures of product $A_1$ from Example 2 with a product $A_2+B_2$ prepared according to the technique described in EP 136,230 and whose composition by weight relative to the general formula was the following:

| | |
|---|---|
| (i) 75% of oligomer $A_2$ | $q_1$ and $q_2 = 0$; |
| (ii) 23% of oligomer $A_2$ | $q_1 = 1$ and $n_2 = 0$ and | of oligomers $B_2$
$q'_1=q'_2=q''_1=q''_2=q_3=q'_3=q_4=q_5=0$;

| | |
|---|---|
| (iii) 2% of oligomers $A_2$ | $q_1 = q_2 = 1$ and | of oligomers $B_2$
$q'_1+q'_2+q''_1+q''_2+q_3+q'_3+q_4+q_5=1$.

The content of oligomers $B_2$:

$q'_1=q'_2=q''_1=q''_2=q_3=q'_3=q_4=q_5=0$ was 2.5%, determined by chromatographic analysis.

The crystallization point was below $-40°$ C. The viscosity at 20° C. was 6.5 cP and the relative density 1.006.

| | Weight composition | Start of crystallization |
|---|---|---|
| Product $A_1$ | 100 | $-3°$ C. |
| Product $A_1$ | 90 | $-5°$ C. |
| Product $A_2 + B_2$ | 10 | |
| Product $A_1$ | 80 | $-10°$ C. |
| Product $A_2 + B_2$ | 20 | |
| Product $A_1$ | 50 | $-30°$ C. |
| Product $A_2 + B_2$ | 50 | |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A dielectric composition of matter comprising admixture of the two oligomers $A_1$ and $A_2$, wherein:
   (i) $A_1$ comprises an isomer or mixture of isomers of the formula:

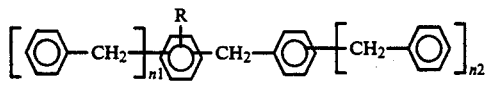

in which $n_1$ and $n_2 = 0$, 1 or 2, with the proviso that $n_1 + n_2$ is less than or equal to 3 and R is a hydrogen atom; and
   (ii) $A_2$ comprises an isomer or mixture of isomers of the same formula as $A_1$, except that R is methyl and $n_1$ and $n_2$ are designated $q_1$ and $q_2$ but have the same values, and with the further proviso that at least one of the oligomers $A_1$ and $A_2$ comprises an isomer having three benzene nuclei.

2. The dielectric composition as defined by claim 1, wherein $n_1 = n_2 = 0$ in the oligomer $A_1$ and $q_1 + q_2 = 1$ in the oligomer $A_2$.

3. The dielectric composition as defined by claim 1, wherein $n_1 + n_2 = 1$ in the oligomer $A_1$ and $q_1 = q_2 = 0$ in the oligomer $A_2$.

4. The dielectric composition as defined in claim 1, wherein $n_1 + n_2 = 1$ in the oligomer $A_1$ and $q_1 + q_2 = 1$ in the oligomer $A_2$.

5. The dielectric composition as defined by claim 1, further comprising at least one of the following oligomers $B_1$, $B_2$ and $B_3$:
   (iii) $B_1$ which comprises an isomer or mixture of isomers of the formula:

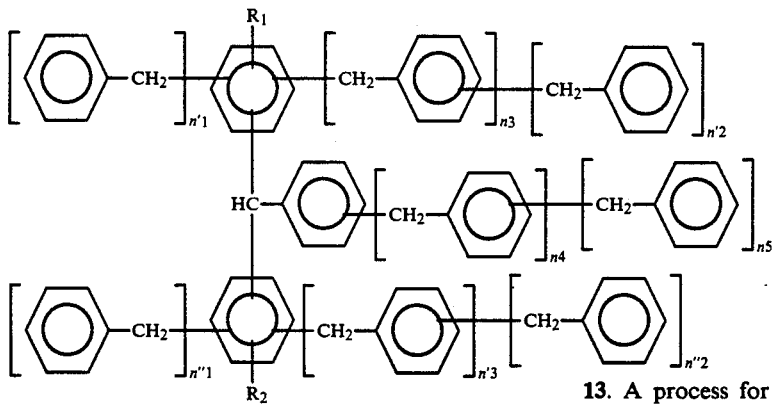

in which $n'_1$, $n''_1$ and $n_4 = 0$, 1 or 2 and $n'_2$, $n''_2$, $n_3$, $n'_3$ and $n_5 = 0$ or 1, with the proviso that $n'_1 + n''_1 + n'_2 + n''_2 + n_3 + n'_3 + n_4 + n_5$ is less than or equal to 2, and $R_1$ and $R_2$ are each a hydrogen atom;
   (iv) $B_2$ which comprises an isomer or mixture of isomers of the same formula as $B_1$, except that $R_1$ and $R_2$ are methyl and the coefficients n are designated as q but have the same values; and
   (v) $B_3$ which comprises an isomer or mixture of isomers of the same formula as $B_1$, except that $R_1$ and $R_2$ are different, one being a hydrogen atom and the other methyl and the coefficients n are designated as r, but have the same values.

6. The dielectric composition as defined by claim 5, comprising the oligomers $A_1$, $A_2$ and $B_2$.

7. The dielectric composition as defined by claim 5, comprising the oligomers $A_1$, $A_2$, $B_1$, $B_2$ and $B_3$.

8. A process for the preparation of the mixture $A_1 + B_1$ as defined in claim 5, comprising:
   (a) reacting chlorine with a mixture of benzene and toluene via radical reaction in the presence of a free radical generator;
   (b) removing the unreacted toluene; and
   (c) treating the product of reaction with an inorganic halide or an inorganic acid.

9. A process for the preparation of the mixture $A_1 + B_2$ as defined in claim 5, comprising:
   (a) reacting chlorine with toluene via radial reaction in the presence of a free radical generator;
   (b) removing the unreacted toluene; and
   (c) adding benzene to the product of reaction and treating it with an inorganic halide or an inorganic acid.

10. A process for the preparation of the dielectric composition as defined by claim 1, comprising reacting benzyl chloride with benzene and toluene in the presence of an organic halide or an inorganic acid.

11. A process for the preparation of the dielectric composition as defined by claim 1, comprising:
    (a) reacting chlorine with toluene and benzene in the presence of a free radical generator;
    (b) removing benzylidene chloride therefrom; and
    (c) treating the product of reaction with an inorganic halide or an inorganic acid.

12. A process for the preparation of the dielectric composition as defined by claim 1, comprising:
    (a) reacting chlorine with toluene in the presence of a free radical generator;
    (b) removing benzylidene chloride therefrom; and
    (c) adding benzene to the product of reaction and treating it with an inorganic halide or an inorganic acid.

13. A process for the preparation of the dielectric composition as defined by claim 7, comprising:
    (a) reacting chlorine with a mixture of benzene and toluene via radical reaction in the presence of a free radical generator; and
    (b) treating the product of reaction with an inorganic halide or an inorganic acid.

14. In a capacitor including a dielectric fluid, the improvement which comprises, as the dielectric fluid therefor, the dielectric composition as defined by claim 1.

15. In a capacitor including a dielectric fluid, the improvement which comprises, as the dielectric fluid therefor, the dielectric composition as defined by claim 5.

16. The dielectric composition as defined by claim 1, wherein $A_2$ comprises from 60% to 80% by weight of the total amount of $A_1 + A_2$.

* * * * *

UNITED STATES PATENT AND TRADEMARK OFFICE
CERTIFICATE OF CORRECTION

PATENT NO. : 5,192,463
DATED : March 9, 1993
INVENTOR(S) : Berger et al

It is certified that error appears in the above-indentified patent and that said Letters Patent is hereby corrected as shown below:

Column 9, line 4, delete "(1,266g)",
Column 10, line 55, in Example 5, "-3°C" should be --+3°C--.

Signed and Sealed this

Fifth Day of April, 1994

BRUCE LEHMAN

Attest:

Attesting Officer          Commissioner of Patents and Trademarks